United States Patent [19]
Abplanalp

[11] Patent Number: 4,595,391
[45] Date of Patent: Jun. 17, 1986

[54] OINTMENT APPLICATOR

[76] Inventor: George Abplanalp, 1037 Rosedale Rd., Venice, Fla. 33595

[21] Appl. No.: 569,726

[22] Filed: Jan. 10, 1984

[51] Int. Cl.⁴ ............................................. A61F 7/02
[52] U.S. Cl. ................................... 604/308; 604/897
[58] Field of Search .............. 604/308, 304, 307, 897, 604/289; 128/156

[56] References Cited

U.S. PATENT DOCUMENTS

| | | | |
|---|---|---|---|
| 2,858,830 | 10/1956 | Robins | 604/308 X |
| 3,882,867 | 5/1975 | Moran | 604/308 X |
| 4,486,194 | 12/1984 | Ferrara | 604/308 X |

Primary Examiner—Stephen C. Pellegrino
Attorney, Agent, or Firm—Hauke and Patalidis

[57] ABSTRACT

A medication ointment applicator comprising a length of plastic film to which is attached a backing made of a length of elastic mesh material. The ointment is applied to the surface of the plastic film which is engaged with the skin of the user, the elastic material backing being wrapped around, for example, the user's ankle or wrist such as to hold the plastic film in firm engagement with the skin for absorption of the medication ointment through the skin. Preferably, the plastic film is provided with a scale enabling the user to measure the amount of ointment being applied as a result of measuring the length of a ribbon of ointment expelled from a dispenser tube, and the surface of the plastic film to which the ointment is applied is textured, for example, by ridges being formed on the surface, to help contain the ointment within the edges of the plastic film. The band of elastic mesh material is provided with fastening means such as, for example, a patch of hook and loop material on one end and lateral strips of complementary hook and loop material at the other end such that the backing of elastic mesh material can be wrapped tight and held in position around the limb of a person.

12 Claims, 6 Drawing Figures

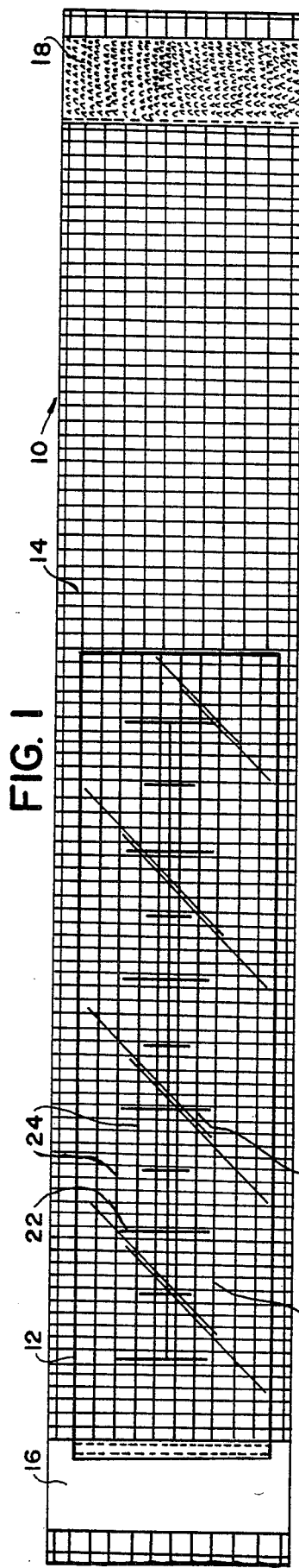
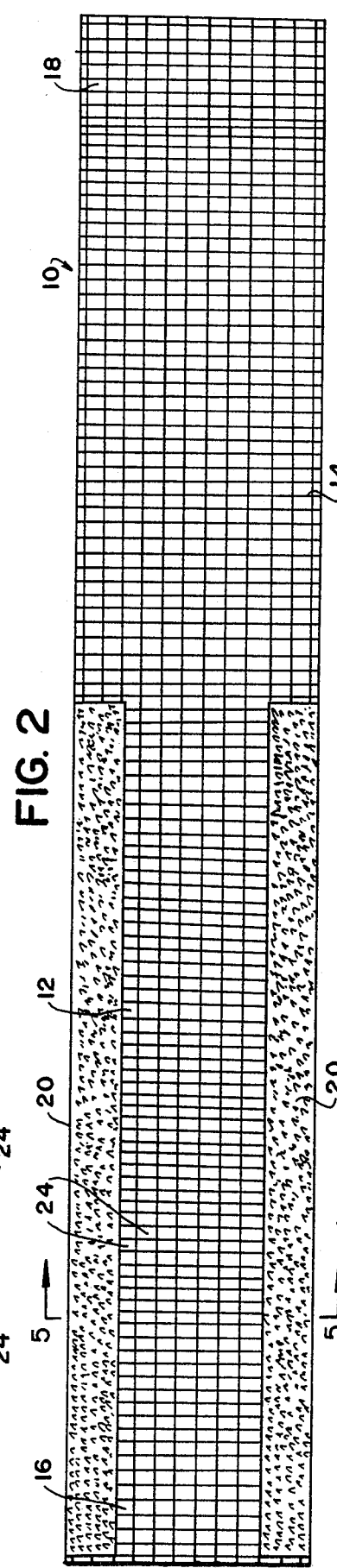
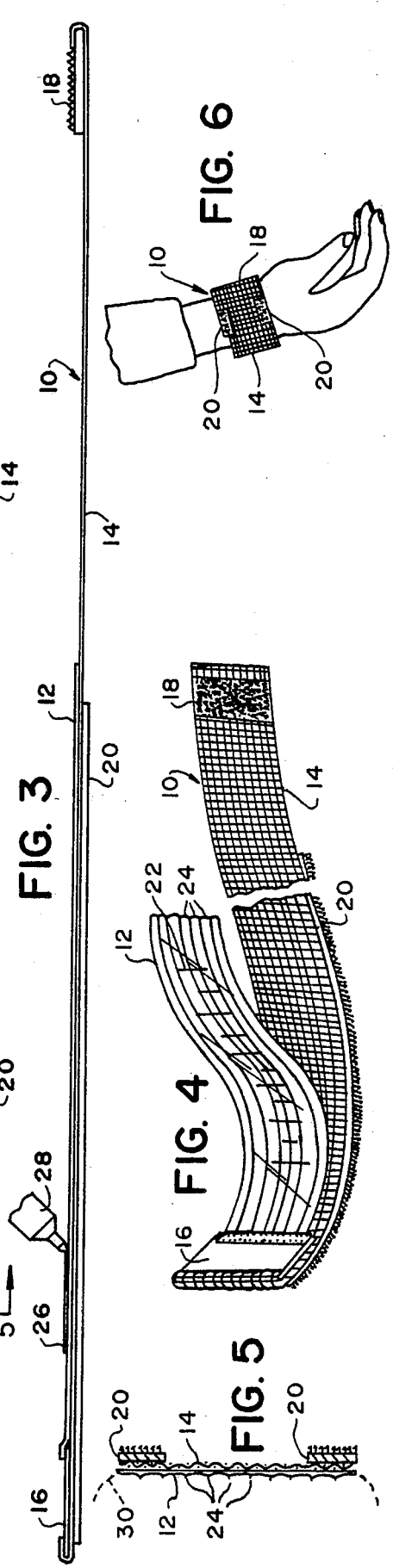

OINTMENT APPLICATOR

BACKGROUND OF THE INVENTION

The present invention relates to a medication ointment applicator.

Medication in the form of an ointment is often dispensed from a container to a bandage which is in turn attached to an area of the body of a patient. The bandage is attached by any convenient means, such as by adhesive tapes, and the medication ointment is slowly absorbed through the skin.

More particularly, nitroglycerine ointment is often dispensed to cardiac patients in the form of an ointment absorbed through the skin. The ointment is dispensed from a tube-like container to a paper applicator. The paper applicator has a printed scale on one surface, and the ointment is squeezed from the neck of the tube-type container in a measured length such as to dispense a prescribed dosage of medication. The paper applicator is translucent such that the printed scale can be seen through the sheet of paper, and the ribbon of ointment dispensed from the tube-type container is applied to the non-printed side of the paper applicator, to prevent contamination of the ointment by the ink used for printing the scale.

The paper applicator is attached by adhesive tape to an area of the body, such as the wrist, the arm, or the ankle, and remains in position until the ointment has been absorbed by the patient through the skin. Since a predetermined dosage of ointment must often be applied several times a day, sometimes as often as every three or four hours, constant application and removal of adhesive tape applicators is somewhat annoying and time consuming, and leads to skin irritations which may become painful.

SUMMARY OF THE INVENTION

The present invention provides a medication ointment applicator bandage permitting to apply a predetermined dosage of medication ointment, such as nitroglycerine, for example, in a safe, easy and painless manner. The ointment applicator bandage of the invention can be repeatedly used, and does not require any adhesive tape for attachment to an area of a patient's body, is neat in appearance as compared to paper applicators, and prevents seepage of the ointment through the applicator or through the edge of the applicator.

This and other advantages of the present invention will become apparent to those skilled in the art when the following description of the best mode contemplated at the present for the invention is read in conjunction with the accompanying drawing, in which:

DESCRIPTION OF THE DRAWING

FIG. 1 is a schematic front elevation view of a medication ointment applicator bandage according to the present invention;

FIG. 2 is a rear elevation view thereof;

FIG. 3 is a side elevation view thereof;

FIG. 4 is a perspective view thereof;

FIG. 5 is a transverse section thereof along line 5—5 of FIG. 2; and

FIG. 6 is a view showing the medication ointment applicator bandage of the invention in use.

DETAILED DESCRIPTION OF THE PREFERRED EMBODIMENT

Referring to the drawing, a medication ointment applicator bandage 10 according to the present invention comprises an elongated sheet 12 of transparent or translucid plastic film such as ABS, cellulosic or fluoro plastics, polyamide, polypropylene, polyvinyl chloride, polyethylene or ethylene copolymers. The sheet 12 of plastic film is attached at one end to a backing band 14 of elastic mesh material either by being sewn or cemented directly onto it, or through the intermediary of a short band 16 of fabric, as shown. The free end of the band 14 of elastic mesh material is provided with an appropriate fastening means such as, for example, a patch 18 of plastic hook material, such as the material sold under the trademark Velcro, while the back side of the elastic mesh material is provided with a pair of narrow strips 20 of loop-type material attached, such as by sewing, along each lateral edge of the elastic mesh material band 14.

The sheet 12 of plastic film has its rear surface provided with a printed scale 22 disposed along the centerline of the sheet, and visible through the transparent or translucid plastic film. The front surface of the sheet 12 of plastic film is textured, for example and as illustrated, by having a plurality of parallel longitudinally extending ridges 24 being embossed thereon, such as to project from the front surface, as best shown at FIG. 5.

In use, the ointment applicator bandage 10 of the invention is held on a flat surface, as shown at FIG. 3, and a ribbon 26 of ointment such as, for example, glycerine ointment, is applied on the textured surface of the sheet 12 of plastic film, from the neck of a squeezed tube 28. The dosage of ointment can be determined relatively precisely by applying to the textured surface of the plastic film sheet 12, at its center and along the scale 22, a ribbon 26 of ointment of a predetermined length. The ointment applicator bandage 10 is then wrapped around an area of the body such as, for example, the wrist, FIG. 6, with the textured surface of the plastic film sheet 12 carrying the ribbon 26 of ointment in direct contact with the skin, the elastic mesh band 14 being wound around the wrist, relatively tight, and being held in position by the patch 18 of fastener material being applied against a portion of the two strips 20 of complementary loop material. The textured surface of the plastic film sheet 12 provided with longitudinally extending ridges 24 causes the ointment to be captured in the space between consecutive ridges 24 in engagement with a surface 30, FIG. 5, such as the skin of a person, thereby preventing seepage of the ointment in lateral directions beyond the lateral edges of the plastic film sheet 12. If so desired, the textured surface of the plastic film sheet 12 may also be provided with transverse ridges, not shown, such that longitudinal seepage of the ointment beyond the ends of the plastic film sheet 12 is controlled to a certain degree.

After having maintained the applicator bandage 10 over an appropriate area of a patient's body for a prescribed period of time, re-application of the ointment may be effected simply by pulling the end of the elastic band 14 provided with the pad 18 of fastener material such as to separate it from the complementary strips 20 of fastener material, unwrapping the applicator bandage 10, reloading the textured surface of the plastic film sheet 12 with a ribbon of ointment of appropriate length, and wrapping and attaching again the applicator bandage 10 in its original or a different position.

Having thus described the present invention by way of a typical example of structure thereof, modifications whereof will be apparent to those skilled in the art, what is claimed as new is as follows:

1. A medication ointment applicator for applying a predetermined amount of medication ointment to a person's skin, said applicator comprising a band of flat plastic pliable film, a band of elastic material of a greater length than said band of plastic film, said band of plastic film having an end attached proximate an end of said band of elastic material, a scale longitudinally disposed substantially along the centerline of the band of plastic film provided with length graduations for measuring a length of ribbon of medication ointment applied to a surface of said plastic film for engagement with a person's skin, and fastening means at the other end of said band of elastic material for attaching said other end to a portion of said band of elastic material whereby said applicator is wound around a person's limb with said plastic film carrying said ointment in engagement with the skin of said person.

2. The medication ointment applicator of claim 1 wherein said fastening means comprises a patch of hook and loop material attached to said band of elastic material and a pair of marginal strips of complementary hook and loop material attached to the back of said band of elastic material.

3. The medication ointment applicator of claim 2 further comprising a textured surface on said plastic film for preventing excessive spreading of said ointment when said textured surface is applied against a person's skin.

4. The medication ointment applicator of claim 3 wherein said textured surface is formed of a plurality of longitudinally extending parallel ridges on said surface of said plastic film.

5. The medication ointment applicator of claim 4 wherein said elastic material is an elastic mesh material.

6. The medication ointment applicator of claim 2 wherein said elastic material is an elastic mesh material.

7. The medication ointment applicator of claim 3 wherein said elastic material is an elastic mesh material.

8. The medication ointment applicator of claim 1 further comprising a textured surface on said plastic film for preventing excessive spreading of said ointment when said textured surface is applied against a person's skin.

9. The medication ointment applicator of claim 8 wherein said textured surface is formed of a plurality of longitudinally extending parallel ridges on said surface of said plastic film.

10. The medication ointment applicator of claim 9 wherein said elastic material is an elastic mesh material.

11. The medication ointment applicator of claim 8 wherein said elastic material is an elastic mesh material.

12. The medication ointment applicator of claim 1 wherein said elastic material is an elastic mesh material.

* * * * *